United States Patent

Possanza et al.

[11] 3,980,658
[45] Sept. 14, 1976

[54] (INDOLYL-PIPERIDINO OR -1,2,5,6-TETRAHYDRO-PYRIDYL)-p-FLUORO-BUTYROPHENONES AND SALTS THEREOF

[75] Inventors: Genus Possanza, Dorval; Kurt Freter, Beaconsfield, both of Canada; Sven Lüttke, Gau-Algesheim, Germany

[73] Assignee: Boehringer Ingelheim GmbH, Ingelheim am Rhein, Germany

[22] Filed: May 6, 1974

[21] Appl. No.: 467,497

[30] Foreign Application Priority Data
May 4, 1973 Germany............... 23224706

[52] U.S. Cl. .............. 260/293.61; 260/296 B; 424/263; 424/267
[51] Int. Cl.² ....................... C07D 401/04
[58] Field of Search ............ 260/293.61, 296 B

[56] References Cited
UNITED STATES PATENTS

| | | | |
|---|---|---|---|
| 3,501,465 | 3/1970 | Shen et al. .................. | 260/240 |
| 3,527,761 | 9/1970 | Archibald et al. ............ | 260/293 |
| 3,639,414 | 2/1972 | Archer ...................... | 260/295 B |
| 3,850,938 | 11/1974 | Derible et al. .............. | 260/293.61 |

Primary Examiner—G. Thomas Todd
Attorney, Agent, or Firm—Hammond & Littell

[57] ABSTRACT

Compounds of the formula

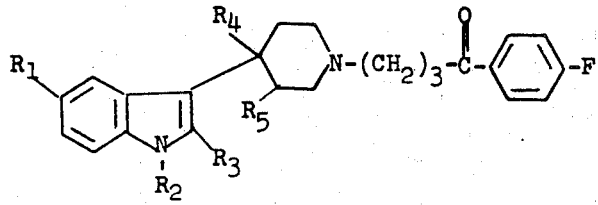

wherein
$R_1$ is hydrogen, chlorine, methyl, methoxy or trifluoromethyl,
$R_2$ is hydrogen or methyl,
$R_3$ is methyl or phenyl, and
$R_4$ and $R_5$ together form a double bond or, in case $R_1$ is chloro, methyl or trifluoromethyl, are also hydrogen atoms,
and non-toxic, pharmacologically acceptable acid addition salts thereof; the compounds as well as their salts are useful as sedatives and tranquilizers.

10 Claims, No Drawings

(INDOLYL-PIPERIDINO OR -1,2,5,6-TETRAHYDRO-PYRIDYL)-P-FLUORO-BUTYROPHENONES AND SALTS THEREOF

This invention relates to novel (indolyl-piperidino or -1,2,5,6-tetrahydro-pyridyl)-p-fluoro-butyrophenones and non-toxic acid addition salts thereof, as well as to methods of preparing these compounds.

More particularly, the present invention relates to a novel class of compounds represented by the formula

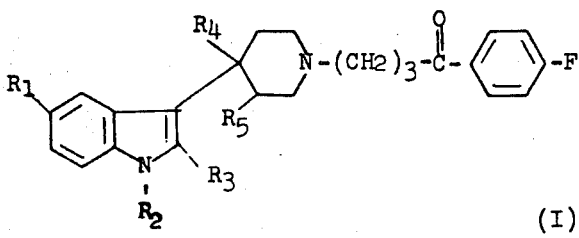

wherein
- $R_1$ is hydrogen, chlorine, methyl, methoxy or trifluoromethyl,
- $R_2$ is hydrogen or methyl,
- $R_3$ is methyl or phenyl, and
- $R_4$ and $R_5$ together form a double bond or, in case $R_1$ is chloro, methyl or trifluoromethyl, are also hydrogen atoms, and non-toxic, pharmacologically acceptable acid addition salts thereof.

The compounds embraced by formula I may be prepared by the following methods:

METHOD A

By alkylating a correspondingly substituted 4-indolyl-piperidine or -tetrahydropyridine of the formula

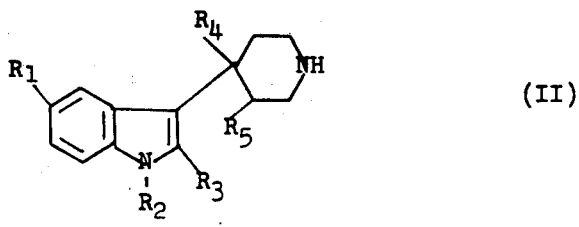

wherein $R_1$, $R_2$, $R_3$, $R_4$ and $R_5$ have the same meanings as in formula I, with an ω-halo-p-fluoro-butyrophenone of the formula

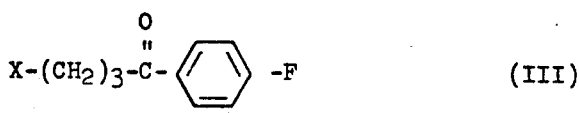

wherein X is halogen.

The alkylation reaction is preferably performed in an inert organic solvent, such as methanol, ethanol, higher alcohols, tetrahydrofuran, dimethylformamide or a mixture of two or more of these solvents, and in the presence of an organic or inorganic base, such as triethylamine, sodium bicarbonate or potassium carbonate. When using ω-chloro-p-fluorobutyrophenone as the alkylating agent, it has proved to be of advantage to add potassium iodide to the reaction mixture.

The optimum reaction temperature and reaction time depend upon the reactivity of the starting materials, but the reaction is preferably effected under reflux.

If in formula II $R_4$ and $R_5$ together represent a double bond, this double bond may, if desired, be hydrogenated either before or after the alkylation.

The hydrogenation subsequent to the alkylation reaction is preferably effected with diimine as the hydrogenation agent. The hydrogenation before alkylation is described below in conjunction with the preparation of the starting materials.

METHOD B

By reacting an indole of the formula

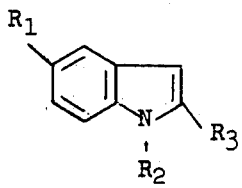

wherein $R_1$, $R_2$ and $R_3$ have the same meanings as in formula I, with 1-(4-p-fluorophenyl-4-oxobutyl)-piperidone-(4)-of the formula

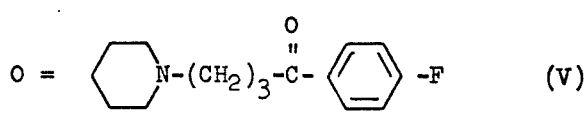

This reaction is effected by heating the two reactants in a mixture of glacial acetic acid and an aqueous mineral acid, preferably phosphoric acid, and yields a 1,2,5,6-tetrahydropyridyl-p-fluoro-butyrophenone of the formula I, which may then, if desired, be hydrogenated to form the corresponding piperidino compound.

The compounds embraced by formula I are organic bases and therefore form acid addition salts with inorganic or organic acids. Examples of non-toxic, pharmacologically acceptable acid addition salts are those formed with a hydrohalic acid, nitric acid, sulfuric acid, orthophosphoric acid, oxalic acid, citric acid, tartaric acid, fumaric acid, maleic acid, propionic acid, butyric acid, acetic acid, methane- or toluene-sulfonic acid, succinic acid, 8-chlorotheophylline or the like.

The starting compounds of the formula II are also new. They may be obtained, for example, by reacting a correspondingly substituted indole of formula IV with the stoichiometric quantity or a slight excess of 4-piperidone in a mixture of glacial acetia acid and phosphoric acid, while heating. The 1,2,5,6-tetrahydropyridine compound thus obtained may then, if desired, be hydrogenated in the presence of platinum/coal or diimine pursuant to conventional methods.

A starting compound of the formula II may also be obtained by reacting an indole of the formula IV in a mixture of glacial acetic acid and phosphoric acid with the equivalent quantity of N-acetyl-4-piperidone, preferably at room temperature. The corresponding 4-indolyl-1-acetyl-1,2,5,6-tetrahydropyridine is thus obtained, which is then hydrogenated in conventional manner in the presence of palladium/coal at room temperature and atmospheric pressure to form the corresponding piperidine derivative; the latter is subsequently hydrolized in a mixture of a lower alkanol and aqueous 50% potassium hydroxide.

Examples of specific end products which may be prepared by means of methods A and B are the following:

4-[4'-(5''-chloro-2''-methyl-3''-indolyl)-piperidino]-p-fluorobutyrophenone,

4-[4'-(5''-chloro-2''-methyl-3''-indolyl)-1',2',5',6'-tetrahydro-1'-pyridiyl]-p-fluoro-butyrophenone, 4-[4'-(5''-methoxy-2''-methyl-3''-indolyl)-1',2',5',6'-tetrahydro-1'-pyridyl]-p-fluoro-butyrophenone, 4-[4'-(1'',2''-dimethyl-3''-indolyl)-1',2',5',6'-tetrahydro-1'-pyridyl]-p-fluoro-butyrophenone, 4-[4'-(2''-methyl-3''-indolyl)-1',2',5',6'-tetrahydro-1'-pyridyl]-p-fluoro-butyrophenone, 4-[4'-(5''-chloro-1'',2''-dimethyl-3''-indolyl)-1',2',5',6'-tetrahydro-1'-pyridyl]-p-fluoro-butyrophenone, 4-[4'-(2'',5''-dimethyl-3''-indolyl)-1',2',5',6'-tetrahydro-1'-pyridyl]-p-fluoro-butyrophenone, 4-[4'-(1''-methyl-2''-phenyl-3''-indolyl)-1',2',5',6'-tetrahydro-1'-pyridyl]-p-fluoro-butyrophenone, and 4-[4'-(5''-trifluoromethyl-2''-methyl-3''-indolyl)-piperidino]-p-fluoro-butyrophenone.

The following examples illustrate the present invention and will enable others skilled in the art to understand it more completely. It should be understood, however, that the invention is not limited solely to the particular examples given below.

EXAMPLE 1

4-[4'-(5''-chloro-2''-methyl-3''-indolyl)-1',2',5',6'-tetrahydro-1'-pyridyl]-p-fluoro-butyrophenone by method A A mixture of 12.4 gm (0.05 mol) of 4-(5'-chloro-2'-methyl-3'-indolyl)-1,2,5,6-tetrahydropyridine, 10.2 gm (0.051 mol) of ω-chloro-p-fluoro-butyrophenone, 5.9 gm (0.07 mol) of sodium bicarbonate, 11.7 gm (0.07 mol) of potassium iodide, 75 ml of dimethylformamide and 75 ml of tetrahydrofuran was refluxed for two hours. After cooling, the resulting solution was evaporated in vacuo to dryness, and the residue was distributed between a mixture of aqueous sodium bicarbonate and ethyl acetate. The organic layer was separated, washed with a saturated aqueous sodium chloride solution, dried and evaporated to dryness. The residue was recrystallized from ethanol, yielding 12.7 gm (62% of theory) of the compound of the formula

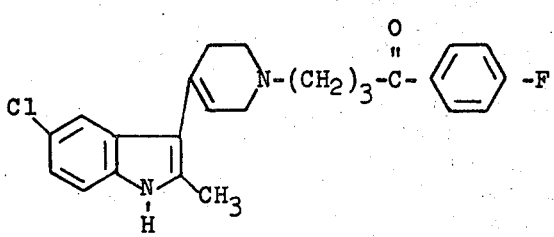

which had a melting point of 83°–87°C.

Its hydrochloride, prepared from the free base in conventional manner, had a melting point of 221°–223°C.

EXAMPLE 2

4-[4'-(5''-chloro-2''-methyl-3''-indolyl)-piperidino]-p-fluoro-butyrophenone by method A A mixture of 29.2 gm (0.1 mol) of 4-(5'-chloro-2'-methyl-3'-indolyl)-piperidine, 20.4 gm (0.1 mol) of ω-iodo-p-fluoro-butyrophenone, 11.8 gm (0.14 mol) of sodium bicarbonate, 23.4 gm (0.14 mol) of potassium iodide, 150 ml of dimethylformamide and 150 ml of tetrahydrofuran was refluxed for 2 hours. After cooling, the resulting solution was evaporated to dryness, and the residue was distributed between a mixture of aqueous sodium bicarbonate and ethyl acetate. The organic layer was separated, washed with a saturated aqueous sodium chloride solution, dried and evaporated. The residue was recrystallized from ethanol, yielding 25.9 gm (73% of theory) of the compound of the formula

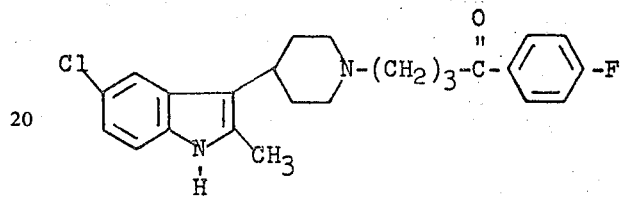

which had a melting point of 190-194°C.

Its methanesulfonate had a melting point of 257°C.

The starting compounds of Examples 1 and 2, 4-(5'-chloro-2'-methyl-3'-indolyl)-1,2,5,6-tetrahydropyridine and 4-(5'-chloro-2'-methyl-3'-indolyl)-piperidine, were prepared as follows:

a. A mixture consisting of 100 gm (0.6 mol) of 5-chloro-2-methyl-indole, 100 gm (0.65 mol) of 4-piperidone monohydrate hydrochloride, 900 ml of glacial acetic acid and 450 ml of 4 N phosphoric acid was heated for 2 hours at 80°C. Thereafter, the reaction mixture was cooled and then poured into a mixture of ice and ammonia, and the resulting mixture was extracted with ethyl acetate. The organic extract solution was washed with water, dried and evaporated, and the residue was recrystallized from methanol, yielding 108 gm (73% of theory) of 4-(5'-chloro-2'-methyl-3'-indolyl)-1,2,5,6-tetrahydropyridine, m.p. 208-210°C.

b. 24.7 gm (0.1 mol) of 4-(5'-chloro-2'-methyl-3'-indolyl)-1,2,5,6-tetrahydropyridine were dissolved in 250 ml of acetic acid, and the solution was hydrogenated at 50°C and a pressure of 5 atmospheres gauge in the presence of 4 gm of 5% platinum on charcoal as a catalyst. The hydrogenation was complete after about 2 hours, whereupon the catalyst was filtered off, the filtrate was evaporated to dryness in vacuo, and the residue was recrystallized from isopropanol. 24.8 gm (80% of theory) of 4-(5'-chloro-2'-methyl-3'-indolyl)-piperidine acetate, m.p. 225°–229°C, were obtained. The free base, m.p. 219°–221°C, was liberated from the acetate with potassium hydroxide.

EXAMPLE 3

Using a procedure analogous to that described in Example 1, 4-[4'-(5''-methoxy-2''-methyl-3''-indolyl)-1',2',5',6'-tetrahydro-1'-pyridyl]-p-fluoro-butyrophenone, m.p. 45°C, of the formula

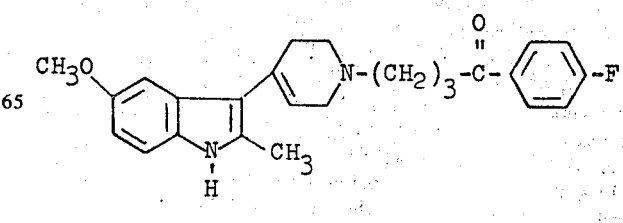

was prepared from 4-(5'-methoxy-2'-methyl-3'-indolyl)-1,2,5,6-tetrahydropyridine and ω-chloro-p-fluoro-butyrophenone.

The starting compound, 4-(5'-methoxy-2'-methyl-3'-indolyl)-1,2,5,6-tetrahydropyridine, was prepared in a manner analogous to that described in a) above from 5-methoxy-2-methyl-indole and 4-piperidone monohydrate hydrochloride.

EXAMPLE 4

Using a procedure analogous to that described in Example 1, 4-[4'-(1'',2''-dimethyl-3''-indolyl)-1',2',5',6'-tetrahydro-1'-pyridyl]-p-fluoro-butyrophenone of the formula

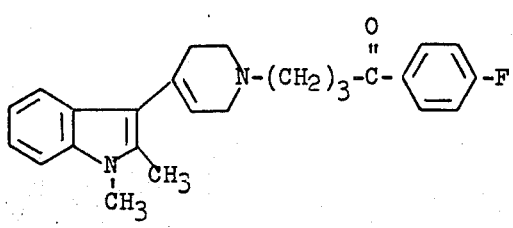

was prepared from 4-(1',2'-dimethyl-3'-indolyl)-1,2,5,6-tetrahydropyridine and ω-chloro-p-fluoro-butyrophenone.

Its hydrochloride had a melting point of 220°C.

The starting compound, 4-(1',2'-dimethyl-3'-indolyl)-1,2,5,6-tetrahydropyridine, was prepared in a manner analogous to that described in (a) above from 1,2-dimethyl-indole and 4-piperidone monohydrate hydrochloride.

EXAMPLE 5

Using a procedure analogous to that described in Example 1, 4-[4'-(2''-methyl-3''-indolyl)-1',2',5',6'-tetrahydro-1'-pyridyl]-p-fluoro-butyrophenone of the formula

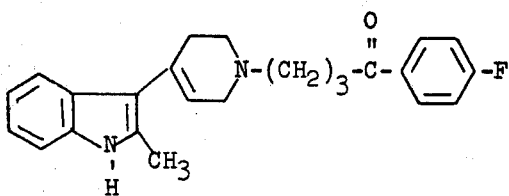

was prepared from 4-(2'-methyl-3'-indolyl)-1,2,5,6-tetrahydropyridine and ω-chloro-p-fluoro-butyrophenone.

Its hydrochloride had a melting point of 208°–210°C.

The starting compound, 4-(2'-methyl-3'-indolyl)-1,2,5,6-tetrahydropyridine, was prepared in a manner analogous to that described in a) above from 2-methyl-indole and 4-piperidone monohydrate hydrochloride.

EXAMPLE 6

Using a procedure analogous to that described in Example 1, 4-[4'-(5''-chloro-1'', 2''-dimethyl-3''-indolyl)-1',2',5',6'-tetrahydro-1'-pyridyl]-p-fluoro-butyrophenone of the formula

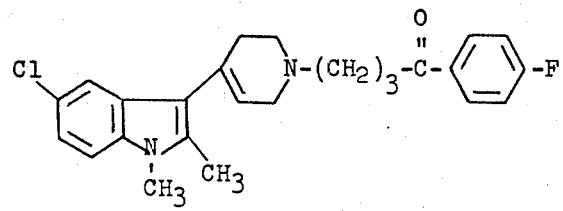

was prepared from 4-(5'-chloro-1',2'-dimethyl-3'-indolyl)-1,2,5,6-tetrahydropyridine and ω-chloro-p-fluoro-butyrophenone.

Its hydrochloride had a melting point of 197°–198°C.

The starting compound, 4-(5'-chloro-1',2'-dimethyl-3'-indolyl)-1,2,5,6-tetrahydropyridine, was prepared in a manner analogous to that described in (a) above from 5-chloro-1,2-dimethyl-indole and 4-piperidone monohydrate hydrochloride.

EXAMPLE 7

Using a procedure analogous to that described in Example 1, 4-[4'-(2'',5''-dimethyl-3''-indolyl)-1',2',5',6'-tetrahydro-1'-pyridyl]-p-fluoro-butyrophenone of the formula

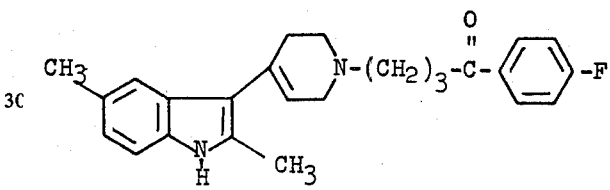

was prepared from 4-(2',5'-dimethyl-3'-indolyl)-1,2,5,6-tetrahydropyridine and ω-chloro-p-fluoro-butyrophenone.

Its hydrochloride had a melting point of 148-151°C.

The starting compound, 4-(2',5'-dimethyl-3'-indolyl)-1,2,5,6-tetrahydropyridine, was prepared in manner analogous to that described in (a) above from 2,5-dimethyl-indole and 4-piperidone monohydrate hydrochloride.

EXAMPLE 8

Using a procedure analogous to that described in Example 1, 4-[4'-(1'''-methyl-2''-phenyl-3''-indolyl)-1',2',5',6'-tetrahydro-1'-pyridyl]-p-fluoro-butyrophenone of the formula

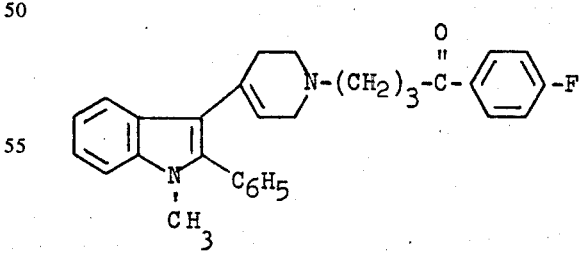

was prepared from 4-(1'-methyl-2'-phenyl-3'-indolyl)-1,2,5,6-tetrahydropyridine and ω-chloro-p-fluoro-butyrophenone.

Its hydrochloride has a melting point of 195°–205°C.

The starting compound, 4-(1'-methyl-2'-phenyl-3'-indolyl)-1,2,5,6-tetrahydropyridine, was prepared in a manner analogous to that described in (a) above from 1-methyl-2-phenyl-indole and 4-piperidone monohydrate hydrochloride.

The compounds of the present invention, that is, those embraced by formula I and their non-toxic, pharmacologically acceptable acid addition salts, have useful pharmacodynamic properties. More particularly, the compounds of this invention exhibit CNS-depressing, sedative and tranquilizing activities, in warm-blooded animals, such as mice and rats.

The CNS-depressing activity of the compounds of the present invention is about the same as that of haloperidol, i.e. 4-[4'-(p-chlorophenyl)-4'-hydroxypiperidino]-p-fluorobutyrophenone, but their toxicities are considerably lower. Thus, while the $LD_{50}$ of haloperidol is about 170 mgm/kg p.o., the $LD_{50}$ of the compounds according to the present invention is far greater than 700 mgm/kg p.o. and in some instances even greater than 1000 mgm/kg p.o.

For pharmaceutical purposes the compounds according to the present invention are administered to warm-blooded animals perorally, parenterally or rectally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like. One effective dosage unit of the compounds according to the present invention is from 0.016 to 0.033 mgm/kg body weight.

The following examples illustrate a few pharmaceutical dosage unit compositions comprising a compound of the present invention as an active ingredient and represent the best modes contemplated of putting the invention into practical use. The parts are parts by weight unless otherwise specified.

EXAMPLE 9

Coated pills

The pill core composition is compounded from the following ingredients:

| | |
|---|---|
| 4-[4'-(5''-Chloro-2''-methyl-3''-indolyl)-piperidino]-p-fluoro-butyrophenone | 2.0 parts |
| Lactose | 28.5 parts |
| Corn starch | 17.0 parts |
| Gelatin | 2.0 parts |
| Magnesium stearate | 0.5 parts |
| Total | 50.0 parts |

Preparation:

The butyrophenone compound is admixed with the lactose and the corn starch, the mixture is granulated with an aqueous 10% solution of the gelatin through a screen of 1 mm mesh-size, dried at 40°C and passed once more through the screen. The granulate thus obtained is admixed with the magnesium stearate, and the composition is compressed into 50 mgm pill cores which are then coated with a thin shell consisting essentially of a mixture of sugar, titanium dioxide, talcum and gum arabic, and polished with beeswax. Each coated pill contains 2 mgm of the butyrophenone compound and is an oral dosage unit composition with effective CNS-depressing action.

EXAMPLE 10

Tablets

The tablet composition is compounded from the following ingredients:

| | |
|---|---|
| 4-[4'-(5''-Chloro-2''-methyl-3''-indolyl)-1',2',5',6'-tetrahydro-1'-pyridyl]-p-fluoro-butyrophenone | 2.0 parts |
| Lactose | 55.0 parts |
| Corn starch | 38.0 parts |
| Soluble starch | 4.0 parts |
| Magnesium stearate | 1.0 parts |
| Total | 100.0 parts |

Preparation:

The butyrophenone compound and the magnesium stearate are admixed, the mixture is granulated with an aqueous solution of the soluble starch, and the granulate is dried and intimately admixed with the lactose and the corn starch. The composition is then compressed into 100 mgm-tablets. Each tablet contains 2 mgm of the butyrophenone compound and is an oral dosage unit composition with effective CNS-depressing action.

EXAMPLE 11

Suppositories

The suppository composition is compounded from the following ingredients:

| | |
|---|---|
| 4-[4'-(5''-Methoxy-2''-methyl-3''-indolyl)-1',2',5',6'-tetrahydro-1'-pyridyl]-p-fluoro-butyrophenone | 1.0 parts |
| Suppository base (e.g. cocoa butter) | 1699.0 parts |
| Total | 1700.0 parts |

Preparation:

The finely pulverized butyrophenone compound is blended with the aid of an immersion homogenizer into the suppository base which had previously been melted and cooled to 40°C. The composition is then cooled to 35°C, and 1700 mgm-portions thereof are poured into cooled suppository molds and allowed to harden therein. Each suppository contains 1 mgm of the butyrophenone compound and is a rectal dosage unit composition with effective CNS-depressing action.

EXAMPLE 12

Hypodermic solution

The solution is compounded from the following ingredients:

| | | |
|---|---|---|
| 4-[4'-(1''',2''-Dimethyl-3''-indolyl)-1',2',5',6'-tetrahydro-1'-pyridyl]-p-fluoro-butyrophenone | | 2.0 parts |
| Sodium chloride | | 18.0 parts |
| Distilled water | q.s.ad | 2000.0 parts by vol. |

Preparation:

The butyrophenone compound and the sodium chloride are dissolved in the distilled water, the solution is filtered until free from suspended particles, and the filtrate is filled into 2 cc-ampules under aseptic conditions. Finally, the ampules are sterilized and sealed. Each ampule contains 2 mgm of the butyrophenone compound, and its contents are an injectable dosage unit composition with effective CNS-depressing action.

Analogous results are obtained when any one of the other compounds embraced by formula I or a non-toxic, pharmacologically acceptable acid addition salt thereof is substituted for the particular butyrophenone derivative in Examples 10 through 13. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to to others skilled in the art that the invention is not limited to these particular embodiments, and that various changes and modifications may be made without departing from the spirit of the invention or the scope of the appended claims.

We claim:

1. A compound of the formula

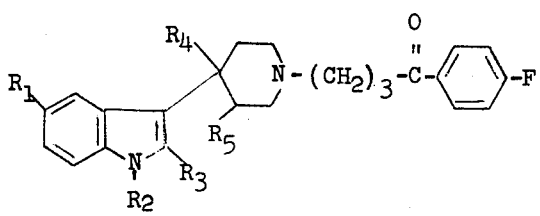

wherein
$R_1$ is hydrogen, chlorine, methyl or methoxy,
$R_2$ is hydrogen or methyl,
$R_3$ is methyl or phenyl, and
$R_4$ and $R_5$ together form a double bond or, when $R_1$ is chlorine or methyl, are also hydrogen, or a non-toxic, pharmacologically acceptable acid addition salt thereof.

2. A compound of claim 1, wherein
$R_1$ is chlorine,
$R_2$ is hydrogen or methyl,
$R_3$ is methyl or phenyl, and
$R_4$ and $R_5$ are hydrogen,
or a non-toxic, pharmacologically acceptable acid addition salt thereof.

3. A compound of claim 1, which is 4-[4'-(5''-chloro-2''-methyl-3''-indolyl)-piperidino]-p-flouro-butyrophenone or a non-toxic, pharmacologically acceptable acid addition salt thereof.

4. A compound of claim 1, which is 4-[4'-(5''-chloro-2''-methyl-3''-indolyl)-1',2',5',6'-tetrahydro-1'-pyridyl]-p-fluoro-butyrophenone or a non-toxic, pharmacologically acceptable acid addition salt thereof.

5. A compound of claim 1, which is 4-[4'-(5''-methoxy-2''-methyl-3''-indolyl)-1',2',5',6'-tetrahydro-1'-pyridyl]-p-fluoro-butyrophenone or a non-toxic, pharmacologically acceptable acid addition salt thereof.

6. A compound of claim 1, which is 4-[4'-(1'',2''-dimethyl-3''-indolyl)-1',2',5',6'-tetrahydro-1'-pyridyl]-p-fluoro-butyrophenone or a non-toxic, pharmacologically acceptable acid addition salt thereof.

7. A compound of claim 1, which is 4-[4'-(2''-methyl-3''-indolyl)-1',2',5',6'-tetrahydro-1'-pyridyl]-p-fluoro-butyrophenone or a non-toxic, pharmacologically acceptable acid addition salt thereof.

8. A compound of claim 1, which is 4-[4'-(5''-chloro-1'',2''-dimethyl-3''-indolyl)-1',2',5',6'-tetrahydro-1'-pyridyl]-p-fluoro-butyrophenone or a non-toxic, pharmacologically acceptable acid addition salt thereof.

9. A compound of claim 1, which is 4-[4'-(2'',5''-dimethyl-3''-indolyl)-1',2',5',6'-tetrahydro-1'-pyridyl]-p-fluoro-butyrophenone or a non-toxic, pharmacologically acceptable acid addition salt thereof.

10. A compound of claim 1, which is 4-[4'-(1'''-methyl-2''-phenyl-3''-indolyl)-1',2',5',6'-tetrahydro-1'-pyridyl]-p-fluoro-butyrophenone or a non-toxic, pharmacologically acceptable acid addition salt thereof.

* * * * *